(12) United States Patent
Safavy

(10) Patent No.: US 7,807,134 B2
(45) Date of Patent: Oct. 5, 2010

(54) MULTIDRUG MULTILIGAND CONJUGATES FOR TARGETED DRUG DELIVERY

(76) Inventor: Ahmad Safavy, 1366 Anglewood Dr., Vestavia Hills, AL (US) 35216

( * ) Notice: Subject to any disclaimer, the term of this patent is extended or adjusted under 35 U.S.C. 154(b) by 0 days.

(21) Appl. No.: 11/959,947

(22) Filed: Dec. 19, 2007

(65) Prior Publication Data

US 2008/0167370 A1     Jul. 10, 2008

Related U.S. Application Data

(62) Division of application No. 10/281,840, filed on Oct. 28, 2002, now Pat. No. 7,311,892.

(60) Provisional application No. 60/348,299, filed on Oct. 26, 2001.

(51) Int. Cl.
| | |
|---|---|
| A61K 51/06 | (2006.01) |
| A61K 38/08 | (2006.01) |
| A61K 38/04 | (2006.01) |
| A61K 39/00 | (2006.01) |
| A61K 39/385 | (2006.01) |

(52) U.S. Cl. .......... 424/1.69; 424/169.1; 424/181.1; 424/193.1; 424/194.1; 424/195.11; 514/15; 514/16; 530/329; 530/391.1

(58) Field of Classification Search .......... None
See application file for complete search history.

(56) References Cited

U.S. PATENT DOCUMENTS

| | | | |
|---|---|---|---|
| 4,863,713 A | | 9/1989 | Goodwin et al. |
| 5,698,178 A | * | 12/1997 | Goldenberg ............... 424/1.49 |
| 5,976,535 A | | 11/1999 | Fritzberg et al. |
| 6,191,290 B1 | | 2/2001 | Safavy |
| 6,200,546 B1 | | 3/2001 | Hoffman |
| 6,287,536 B1 | | 9/2001 | Reno et al. |
| 6,436,386 B1 | | 8/2002 | Roberts et al. |

FOREIGN PATENT DOCUMENTS

| | | |
|---|---|---|
| WO | 98/47524 | 10/1998 |
| WO | 00/78359 A2 | 12/2000 |

OTHER PUBLICATIONS

Dermer et al, Bio/Technology 12: 320, 1994.*
Gura et al, Science 278: 1041-1042, Nov. 1997.*
Pardridge et al, Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration, Pharmaceutical Research 15(4): 576-582, 1998, Plenum Publishing Corporation.
Nathan et al, Copolymers of Lysine and Polyethylene Glycol: A New Family of Functionalized Drug Carriers, Bioconjugate Chem. 4(1): 54-62, Jan.-Feb. 1993, American Chemical Society .
Safavy, A. et al, Paclitaxel Derivatives for Targeted Therapy of Cancer; Toward the Development of Smart Texans, Journal of Medicine Chemistry, 1999, vol. 42, No. 23 : 4919-4924.
Safavy, A. et al, Synthesis of Bombesin Analogues for Radiolabeling with Rhenium-188. Cancer. 1997, vol. 18, No. 12: 2354-2359.
Safavy, A et al, Synthesis Cytotoxicity Evaluation, and Biodistribution Studies of a Novel Paclitasxes-MAb C225 Conjugate, Cancer Biotherapy and Radiopharmaceuticals, 2000, Abstract 8.
Deguchi et al, Retention of Biologic Activity of Human Epidermal Growth Factor Following conjugation to a Blood-Brain Barrier Drug Delivery Vector via an Extended Poly(ethylene glycol) Linker; Bioconjugate Chem 10: 32-37, Jan.-Feb. 1999.
Stryer et al, Biochemistry, Third edition, W H Freeman Company, New York, pp. 31-33, 1998.
Ngo et al, 1994, Computational Complexity, Protein Structure Prediction, and the Levinthal Paradox; the Protein Folding Problem and Tertiary Structure Prediction, pp. 491-495, Birkhauser Boston.
Livnah et al, The Structure of the Complex Between Avidin and the Dye, 2-(4'-hydroxyazobenzene) benzoic acid (HABA), FEBS vol. 328 (1-2): 165-168, Elsevier Science Publishers BV, August 1993.

* cited by examiner

*Primary Examiner*—Phuong Huynh
(74) *Attorney, Agent, or Firm*—Bradley Arant Boult Cummings LLP

(57) ABSTRACT

Described is a multi drug multiligand conjugate for targeted drug delivery. The MDML conjugate contains a plurality of tripartite molecules linked to a central scaffold moiety, with each tripartite molecule comprising a targeting molecule, a therapeutic agent and a scaffold binding element. The MDML conjugate allows for more efficient delivery of therapeutic agents to the cells resulting in enhanced therapeutic efficiency. A model MDL conjugate is disclosed as well as method for the synthesis of the model conjugate.

10 Claims, 6 Drawing Sheets

PTX = Paclitaxel
▽ = Biotin
▽ = Receptor-directed Peptide
∿ = PEG
(S)Av = Avidin or Streptavidin

MULTIDRUG MULTILIGAND CONJUGATES FOR TARGETED DRUG DELIVERY

This application is a divisional of U.S. patent application Ser. No. 10/281,840, filed Oct. 28, 2002, which claims the benefit of U.S. provisional application No. 60/348,229, filed Oct. 26, 2001, now U.S. Pat. No. 7,311,892, issued Dec. 25, 2007. The present disclosure related generally to the field of drug delivery.

BACKGROUND OF THE INVENTION

1. Field of the Invention
2. Description of the Related Art

Targeted drug delivery is a powerful strategy in the treatment and diagnosis of various human diseases, such as cancer, bacterial and viral infections and any disease expressing specific and targetable receptors, antigens or other markers. Targeted drug delivery has gained momentum during the past several years based on the specific delivery therapeutic molecules to malignant tissues comprising the disease state, such as the delivery of oncolytic agent to the neoplastic tissue. The ability to specifically target therapeutic molecules to specific cells of interest has advanced considerably during the past several years with the development of monoclonal antibodies and of synthetic small molecule peptides (SSMPs) capable of binding to tumor cell surface receptors. A number of drug, toxin, and radioisotope conjugates of tumor-recognizing molecules have been developed with some currently in clinical use.

Allergic reactions against large-molecule antibodies in humans due to the immunoreactivity of these proteins have hampered the desired development of antibody-drug conjugates for targeted delivery and much attention has been focused on the SSMPs which usually show no immunoreactivity due to smaller molecular sizes. With the exception of radiolabeled peptides, SSMPs have not been fully utilized as targeting drug delivery systems. Recently, the use of SSMPs in a targeted drug delivery systems with a paclitaxel-bombesin conjugate as a model compound was demonstrated (Safavy, U.S. Pat. No. 6,191,290, 2001; Safavy et al., *J Med Chem*, 1999, 42, 4919-4924). This and similar molecules will be referred to as single drug, single ligand (SDSL) conjugates. While effective at specifically delivering the therapeutic molecule to the target cell of interest, these SDSL conjugates have several limitations. First, the biological half-life of these SDSL conjugates is quite short, with the conjugates undergoing rapid clearance from the circulation (usually on the order of 1 to 5 minutes). As a result, only a fraction of the SDSL conjugates are taken up by the target cells, which results in a low therapeutic efficiency. Secondly, the ability to adapt SDSL conjugates to various disease states or to deliver different therapeutic molecules is limited. It would be beneficial if a conjugate were provided that is designed to deliver different therapeutic molecules to the target cells with a minimum of experimental manipulation.

Therefore, it would be advantageous to provide a pharmaceutical compound for use in a single-step drug delivery method that is capable of specifically delivering to target cells (via a targeting conjugate) multiple copies of the same or different therapeutic agent(s). This approach may result in higher therapeutic indices which may bring about a more significant response from the target cells. The present disclosure provides such a strategy and provides a method for the synthesis of a model conjugate as proof-of principle. This model conjugate was used in a tumor cell proliferation assay to demonstrate the drug-enhancing potential of this approach.

SUMMARY

The present disclosure shows the synthesis and design of two embodiments of a multidrug multiligand (MDML) conjugate which is capable of specifically delivering multiple doses of a therapeutic molecule to a target cell.

In one embodiment of the present disclosure, there is provided a pharmaceutical compound comprising a plurality of tripartite molecules in combination with a scaffold moiety. The tripartite molecules comprises a targeting molecule, a therapeutic agent, a scaffold binding element linked together by a central core molecule, the tripartite molecule being capable of binding to the scaffold moiety through complementary binding between the scaffold binding element and the scaffold moiety.

In another embodiment of the present disclosure, alternate methods of synthesizing the MDML conjugates are described. Specifically, the synthesis of one embodiment of the MDML conjugates, incorporating paclitaxel (a taxane derivative) as the therapeutic agent, a bombesin-derived peptide, BBN [7-13] as the targeting molecule, lysine or diamino benzoic acid as the core molecule and streptavidin/biotin as the scaffold moiety/scaffold binding element (the PTX-BBN [7-13]-BTN/SaV conjugate), is described in detail.

In still yet another embodiment of the present disclosure there is provided a method of treating an individual having a disease by administering the MDML conjugates of the present disclosure to an individual in an amount sufficient to treat the disease. Because of the higher therapeutic index achieved by the MDML conjugates, they may be administered at a lower concentration range than that of the un-conjugated therapeutic agents by means of injection or intravenous infusion. By disease it is meant any abnormal condition of an organ or other part of an organism.

In another embodiment of the present disclosure, there is provided a method of administering the MDML conjugates of the present disclosure to an individual as a diagnostic reagent. Because of the higher therapeutic index achieved by the MDML conjugates, they may be administered at a lower concentration range than that of the un-conjugated therapeutic agents by means of injection or intravenous infusion.

In still another embodiment of the present disclosure, a kit is provided to aid in the treatment of individuals having a particular disease Other and further aspects, features, and advantages of the present disclosure will be apparent from the following description of the presently preferred embodiments of the invention.

BRIEF DESCRIPTION OF THE DRAWINGS

So that the features, advantages and objects of the disclosure will become clear, are attained and can be understood in detail, reference is made to the appended drawings, which are described briefly below. It is to be noted, however, that the appended drawings illustrate preferred embodiments of the disclosure and therefore are not to be considered limiting in their scope.

FIG. 1 shows the synthesis of two embodiments of the PTX-BBN [7-13]-BTN/SaV conjugate, one embodiment of the MDML conjugate of the present disclosure, utilizing paclitaxel (taxol) as the therapeutic agent, a bombesin derivative, BBN [7-13] as the targeting molecule and streptavidin/biotin as the scaffold moiety/scaffold binding element.

DETAILED DESCRIPTION

Figure 1A:
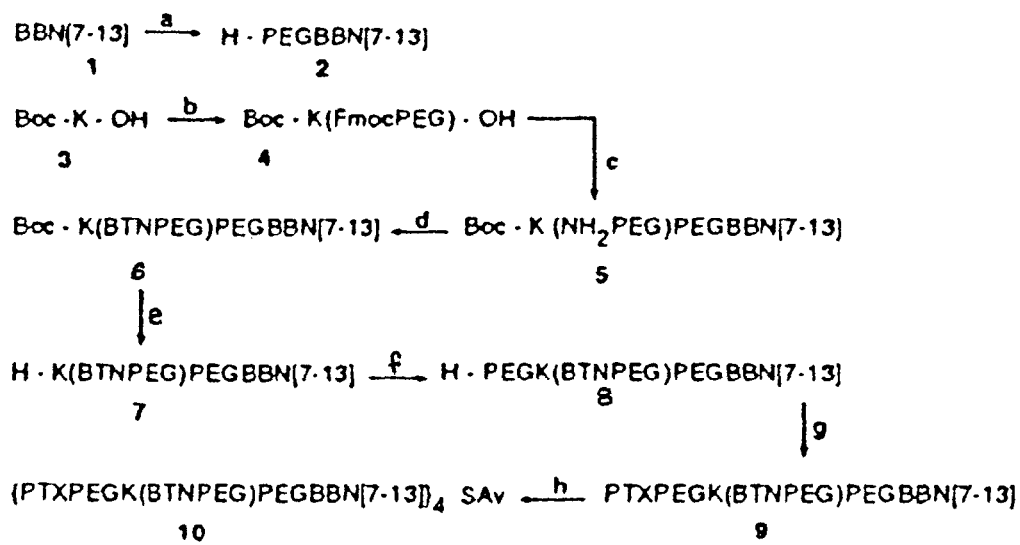
FIG. 1A shows the synthesis of PTX-BBN[7-13]-BTN/SaV using lysine as the core molecule and FIG. 1B shows the synthesis of PTX-BBN[7-13]-BTN/SaV using diamino benzoic acid as the core molecule.

The present disclosure illustrates that the effect of a given therapeutic agent may be enhanced by incorporation of the therapeutic agent into a MDML conjugate capable of delivering a plurality of therapeutic agents to specific target cells of interest by virtue of a plurality of targeting molecules incorporated into the same conjugate. The present disclosure describes methods for the design, synthesis and delivery of MDML conjugates for the treatment of various human disease states. Cancer is the exemplary human disease discussed below and cited in the examples, but this disclosure should not be interpreted to limit only to the treatment of cancer as one of ordinary skill in the art would be able to adapt the teachings of the disclosure to treatment of alternate disease states. It will be understood by those of skill in the art that the MDML conjugate described can be used to treat a variety of disease states by incorporating the desired targeting molecule(s) and therapeutic agent(s).

The MDML conjugate described in the present disclosure comprise a plurality of tripartite molecules in combination with a scaffold moiety. The tripartite molecules each comprise a targeting molecule, a therapeutic agent, a scaffold binding element linked together by a central core molecule. The core molecule provides the framework for construction of the tripartite molecule. The core molecule can be any molecule that provides sufficient functional groups to link together the targeting molecule, the therapeutic agent and the scaffold binding element in a functional manner. The functional groups should be positioned in a manner to minimize steric hindrance between the targeting molecule, the therapeutic agent and the scaffold binding element. In one embodiment, the core molecule is the amino acid lysine. In an alternate embodiment, the core molecule is diamino benzoic acid. Other core molecules may be used as described.

The tripartite molecule is capable of binding to the scaffold moiety through complementary binding between the scaffold binding element and the scaffold moiety. The scaffold moiety provides the framework to join the tripartite molecules together and allows for the delivery of multiple doses of the therapeutic agent to the target cell of interest.

The targeting molecule is any molecule that can direct the MDML conjugate to a defined population of cells of interest (target cells). The targeting molecule may be, but is not limited to, a peptide, a receptor ligand peptide (meaning a peptide that is designed to specifically bind to one or more designated receptor molecules), an antibody or antibody fragment. Exemplary targeting molecules include, but are not limited to, bombesin/gastrin-releasing peptide (BBN/GRP) receptor-recognizing peptide, a somatostatin receptor recognizing peptide, an epidermal growth factor receptor recognizing peptide, a monoclonal antibody or a portion thereof, or polyclonal antibody or a portion thereof, or a receptor recognizing carbohydrate, or any combination of the above. Examples of receptor recognizing polypeptides that bind to the BBN/GRP receptor and/or the somatostatin receptor are the BBN[7-13] (SEQ ID NO. 1) peptide, the BNN[7-14] (SEQ ID NO. 2) peptide and a semi-synthetic derivative of BBN as shown in SEQ ID NO. 3. The targeting molecule incorporated into each tripartite molecule may be the same or may be different. The targeting molecule need not direct the MDML conjugate to only one cell type. The selection of a particular targeting molecule will depend on the cell population to be targeted and is within the ordinary skill in the art.

The therapeutic agent can be any diagnostic agent or any pharmaceutical agent, or a combination thereof. Therapeutic agents include, but not limited to, drugs, anti-tumor agents, toxins, radionuclides, metallic nuclei or a combination of the above. Exemplary therapeutic agents include taxane molecule. By taxane molecule it is meant to include any taxane derivatives such as paclitaxel (taxol) and toxotere (docetaxel) and their analogues. In one embodiment describe, the therapeutic agent is paclitaxel. The therapeutic agent incorporated into each tripartite molecule may be the same or may be different. The selection of a particular therapeutic agent will depend on the particular disease to be treated or condition to be diagnosed and is within the ordinary skill in the art.

The linker molecules may be any molecule capable of linking the targeting molecule, the therapeutic agent and the scaffold binding moiety to a central molecule. The linker molecules may reduce the effects of steric hindrance and increase the overall yield of the synthetic reaction. However, the use of a linker molecule is optional. In the embodiment described polyethylene glycol (PEG) was used as the linker. The chemical and biological properties of PEG molecules have been extensively studied and some useful characteristics of this polymer have been noted. These include aqueous as well as organic solubilities, lack of immunogenicity, and favorable blood clearance patterns and in vivo behavior. Furthermore, PEG molecules are available in a wide range of chemistries, facilitating the formation of the tripartite molecules. In the embodiment disclosed, a heterobifunctional derivative of the PEG was used in this synthesis, allowing the PEG to connect the lysine and targeting molecule, therapeutic agent and scaffold binding moiety as described below in Example 1 and FIG. 1A.

The scaffold binding element and the scaffold moiety may be any set of molecules that are capable of specific, complementary, covalent or non-covalent binding to one another. Exemplary binding pairs include, but are not limited to, poly (amino acids), peptides, polypeptides, proteins, carbohydrates, biotin/avidin, biotin/streptavidin, hapten/antibody, ligand/receptor, enzyme/inhibitor and lectin/carbohydrate. The biotin/streptavidin system has been used in this disclosure as the model scaffold binding element/scaffold moieties. Avidin (isolated from egg whites) and streptavidin (isolated from *Streptomyces avidinii*), each have a very high binding affinity for biotin. The streptavidin-biotin system represents the strongest non-covalent biological interaction known between a protein and a ligand. Streptavidin has a lower non-specific tissue binding and absorption. Both avidin and streptavidin are capable of binding 4 molecules of biotin. Modified forms of avidin and streptavidin may also be used in methods of this disclosure. Biotin includes, but is not limited to biotin which has been modified by the addition of alkyl groups, and biotin derivatives such as active esters, amines, hydrazides and thiol groups with the complimentary reactive groups on polymers being amines, acyl and alkyl leaving groups, carbonyl groups and alkyl halides or Michael-type acceptors.

Figure 3:
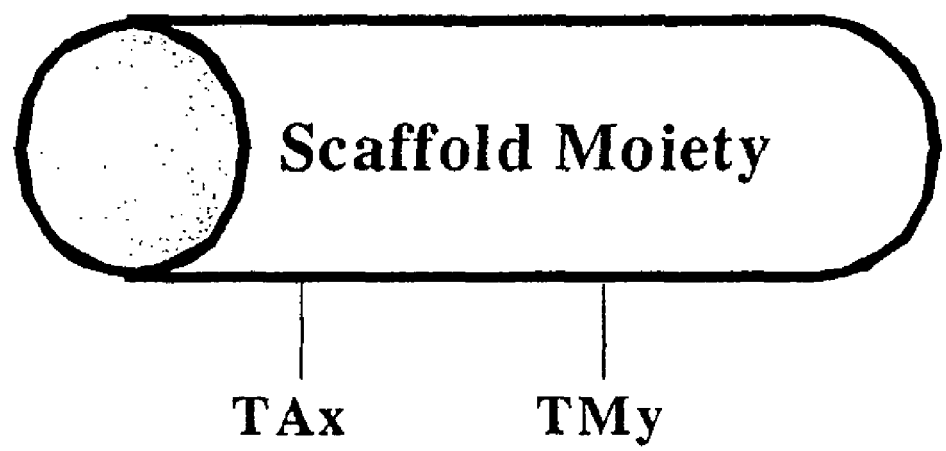
FIG. 3 shows a general schematic representation of the MDML conjugates of the present disclosure.

FIG. 3 shows the generic schematic representation of the MDML conjugates of the present disclosure. The generic MDML conjugates comprise a scaffold moiety to which a plurality of therapeutic agent (Tax, with x being the number of therapeutic molecules attached) and targeting molecules (TMy, with y being the number of targeting molecules attached) are attached via a scaffold binding moiety. The targeting molecules and therapeutic agents can be attached directly to the scaffold moiety, or can be attached to the scaffold moiety through a linker element. Due to steric effects encountered during synthesis, it is preferred that a linker element be employed (shown as a straight line in FIG. 3). The plurality of targeting molecules allow the MDML conjugate to be localized to specific target cells, whereby the plurality of therapeutic agents are delivered to the cell. In this manner, increased concentrations of the therapeutic agents are delivered to the cell, which may bring about a more significant response of the cells to the therapeutic agents. The therapeutic agents attached to the scaffold moiety may be the same or different. The selection of therapeutic agent to be used, and the combination of therapeutic agents to be used if desired, will depend upon the target cell selected. Such selection is within the ordinary skill in the art of those in the field. In the same manner, the selection of the specific targeting molecule (s) to be used will also be determined by the target cell selected. Again, selection of the appropriate targeting molecule is within the ordinary skill in the art of those in the field.

Figure 4:
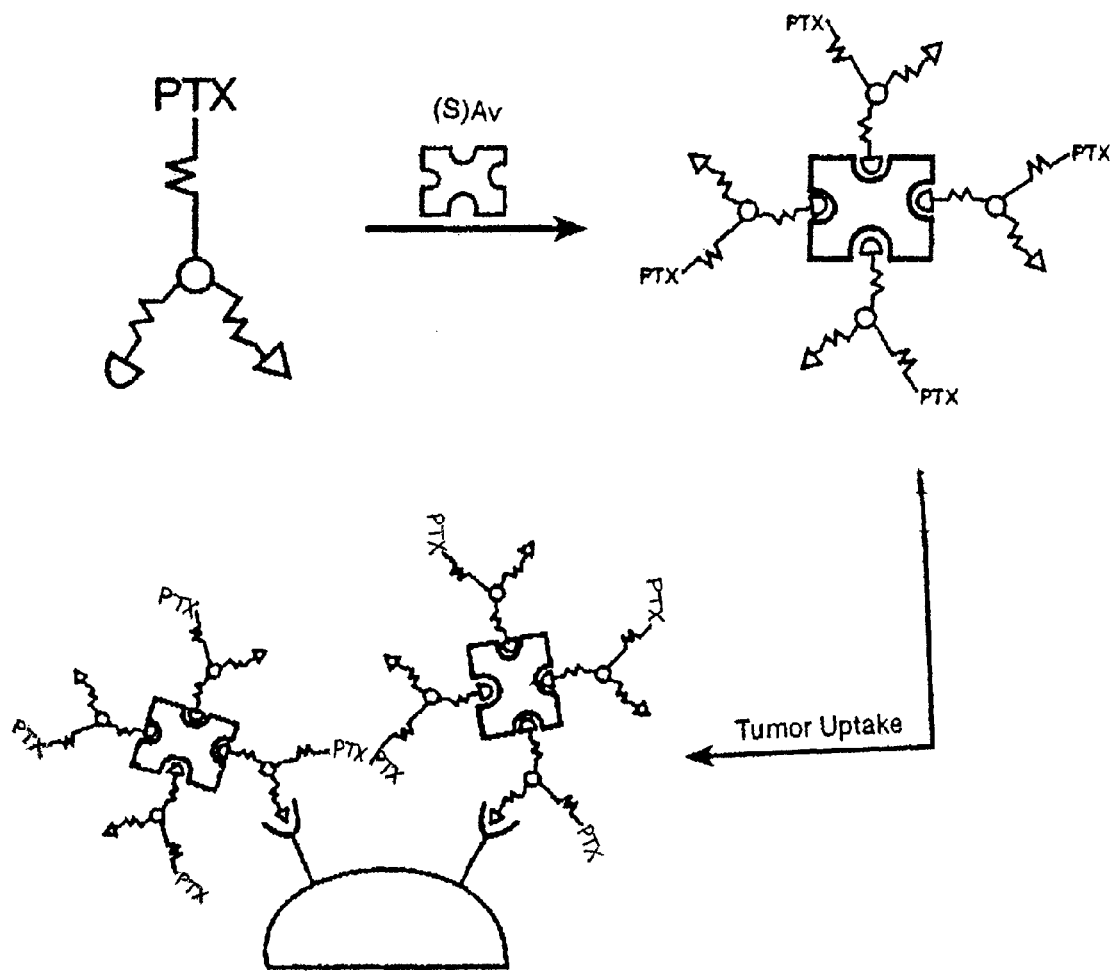
FIG. 4 shows a schematic model of the mechanism of action of the PTX-BBN[7-13]-BTN/SaV MDML conjugate described.

FIG. 4 illustrates a schematic model of tumor uptake of the model MDML conjugate PTX-BBN[7-13]-BTN/SaV. Individual tripartite molecules are synthesized according to the scheme described in FIGS. 1A and 1B and Example 1 below. The tripartite molecules comprise a core molecule to which is covalently linked the bombesin-derived peptide BBN[7-13] which serves as the targeting molecule, paclitaxel, (PTX) as the therapeutic agent and biotin (BTN) as the scaffold binding element. The BBN[7-13], paclitaxel and biotin are linked to the core molecule by PEG linker elements. Once synthesized, the tripartite molecules are joined non-covalently to a streptavidin (SaV) which serves as the scaffold moiety, to form the MDML conjugate PTX-BBN[7-13]-BTN/SaV. As discussed above, the streptavidin scaffold can bind 4 tripartite molecules. The PTX-BBN[7-13]-BTN-SaV conjugate contains multiple copies of the same or different therapeutic agents. In addition, the PTX-BBN[7-13]-BTN-SaV conjugate may contain the same or different targeting molecules. In one embodiment, the same targeting molecules are employed. In an alternate embodiment, different targeting molecules are used, with the different targeting molecules being directed to the same or different target cells. The PTX-BBN[7-13]-BTN-SaV conjugate circulates through the body until BBN[7-13] targeting molecules detect and bind to their binding target on the tumor cell, in this case the bombesin receptor. Once bound to the tumor cell, the therapeutic agents act on the tumor cell through internalization or proximity to the cell, causing cell damage and ultimately cell death.

Figure 5:
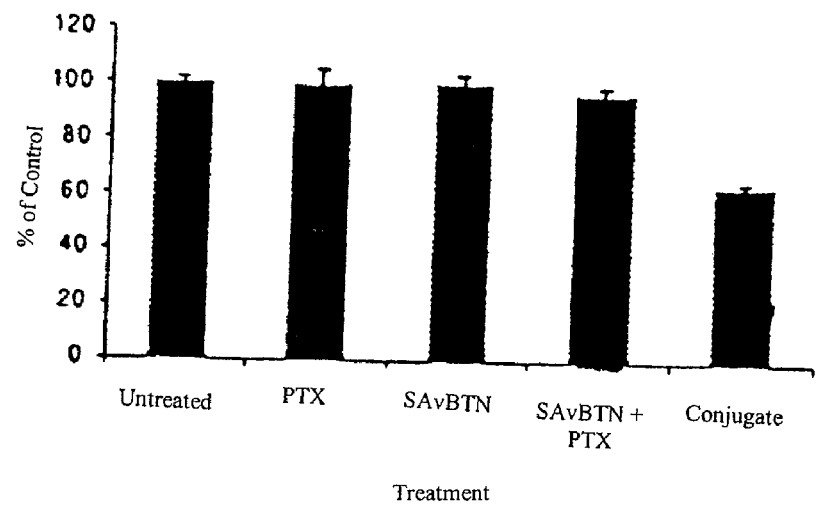
FIG. 5 shows a cell proliferation assay of NCI-H1229 non-small cell lung cancer cells at 4 days post treatment with 50 nM each of the following for three hours: 1) untreated cells (Untreated); 2) unconjugated paclitaxel (PTX); 3) biotin-streptavidin complex (BTN/SaV); 4) a mixture of BTN/SaV and PTX; and 5) the PTX-BBN[7-13]-BTN/SaV conjugate (Conjugate) described in FIG. 1A. The PTX-BBN[7-13]-BTN/SaV conjugate demonstrated 37% growth inhibition compared to 0% growth inhibition by free PTX and untreated cells, and 1% and 4% inhibition by BTN/SaV and BTN/SaV+PTX controls, respectively.
Figure 6:
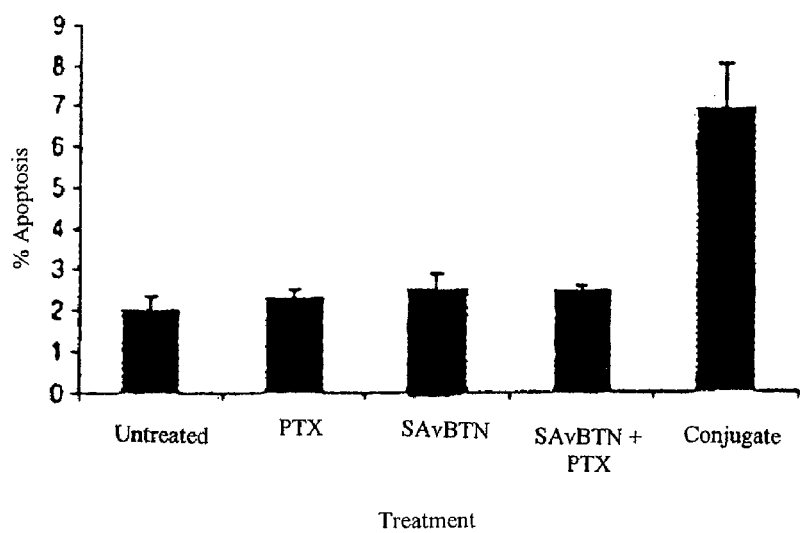
FIG. 6 shows an apoptosis (programmed cell death) induction assay of NCI-H1229 non-small cell lung cancer cells at 4 days post treatment with 50 nM each of the following for three hours: 1) untreated cells (Untreated); 2) unconjugated paclitaxel (PTX); 3) biotin-streptavidin complex (BTN/SaV); 4) a mixture of BTN/SaV and PTX; and 5) the PTX-BBN[7-13]-BTN/SaV conjugate (Conjugate) described in FIG. 1A. Apoptosis was measured by an Annexin V-FITC kit. The PTX-BBN[7-13]-BTN/SaV conjugate showed a 7% induction of apoptosis, as compared to about 2.0%. 2.3%, 2.5% and 2.4% induction for untreated cells, free PTX, the BTN/SaV complex and the BTN/SaV+PTX controls, respectively.

As can be seen in FIGS. 5 and 6, the PTX-BBN[7-13]-BTN-SaV conjugate is active against tumor cells in vitro. FIG. 5 shows a cell proliferation assay demonstrating the sensitivity of native, untransfected NCI-H1299 non-small cell lung cancer cells to the PTX-BBN[7-13]-BTN-SaV conjugate. Cells were grown as described in Example 2 and exposed to various treatments. The cells were left untreated or treated with 50 nM of the PTX-BBN[7-13]-BTN-SaV conjugate, unconjugated paclitaxel (PTX), the biotin/streptavidin complex (BTN/SaV) or a mixture of BTN/SaV and PTX. After 3 hours, the media containing these additives was removed and replaced with fresh media. After 96 hours, the cells were removed from the 24 well plates by treatment with trypsin/EDTA and counted with a Coulter particle counter. All treatments were done in quadruplicate and the cell counts were normalized to the untreated cells. As can be seen in FIG. 5, the PTX-BBN[7-13]-BTN/SaV conjugate inhibited cell growth by 37%, as compared to 0% growth inhibition by free PTX, and 1% and 4% inhibition by BTN/SaV and BTN/SaV+PTX controls, respectively.

FIG. 6 illustrates the results of an apoptosis induction assay, illustrating NCI-HI299 cells are induced to undergo apoptosis specifically in response to the PTX-BBN[7-13]-BTN-SaV conjugate. Cells were grown as described above and in Example 3 and left untreated or treated with 50 nM of the PTX-BBN[7-13]-BTN-SaV conjugate, unconjugated paclitaxel (PTX), the biotin/streptavidin complex (BTN/SaV) or a mixture of BTN/SaV and PTX. After 3 hours, the media containing these additives was removed and replaced with fresh media. After 96 hours, the cells were removed from the 24 well plates by treatment with trypsin/EDTA and analyzed for Annexin V by flow cytometry using an Annexin V-FITC kit (Biovision, Palo Alto, Calif.). All treatments were done in triplicate and presented as the percentage of cells staining with Annexin V-FITC. The PTX-BBN[7-13]-BTN/SaV conjugate showed a 7% induction of apoptosis, as compared to about 2.0%. 2.3%, 2.5% and 2.4% induction for untreated cells, free PTX, the BTN/SaV complex and the BTN/SaV complex+PTX controls, respectively.

The experiments shown in FIGS. 5 and 6 and described in Examples 2 and 3 demonstrate the therapeutic effect of the PTX-BBN[7-13]-BTN/SaV conjugate, and show that the MDML conjugates provide an improved approach to drug delivery and treatment of various disease states. In each of the experiments, the free paclitaxel has no or negligible effect on cell growth or induction of apoptosis, while the PTX-BBN [7-13]-BTN/SaV conjugate was effective in inhibiting cell growth and inducing apoptosis. These results show that specific delivery of multiple therapeutic agents to target cells enhances the effects of the therapeutic agents and serves as an improved method for drug delivery.

Example 1

Synthesis of MDML Conjugate

A MDML conjugate synthesis is described below. The MDML conjugate comprises a plurality of tripartite molecules bound to a scaffold moiety. The tripartite molecules themselves comprise a targeting molecule, a therapeutic agent and a scaffold binding moiety joined together by plurality of linker molecules. Specifically, the synthesis of the PTX-BBN[7-13]-BTN/SaV conjugate is described, where the tripartite molecule comprises paclitaxel (PTX) as the therapeutic agent, a bombesin/gastrin-releasing peptide- (BNN/GRP-) receptor-recognizing peptide (BBN[7-13] SEQ. ID NO. 1) as the targeting molecule and biotin (BTN) as the scaffold binding element and streptavidin (SaV) comprises the scaffold moiety. Two alternate approaches to the synthesis of the PTX-BBN[7-13]-BTN/SaV conjugate are illustrated in FIGS. 1A and 1B.

The synthesis of the tripartite molecules preferably incorporates a linker to join the targeting molecule, therapeutic agent and scaffold binding moiety to a central core, described below as lysine and diamino benzoic acid. The synthesis described below uses polyethylene glycol (PEG) as the linker, although other linker molecules can be used. The linker molecules were used to reduce the effects of steric hindrance and to increase the overall yield of the synthetic reaction. It was determined that a longer chain PEG molecule (3,400 molecular weight) worked well. The chemical and biological properties of polyethylene glycols have been extensively studied and some useful characteristics of this polymer have been noted. These include aqueous as well as organic solubilities, lack of immunogenicity, and favorable blood clearance patterns and in vivo behavior. Furthermore, a heterobifunctional derivative of the PEG was used in this synthesis, allowing the PEG to connect the lysine and targeting molecule, therapeutic agent and scaffold binding moiety. The chemistry and properties of PEG are described in J. M. Harris, Polyethylene Glycol Chemistry: Biotechnical and Biomedical Applications, Plenum, New York, N.Y., 1992; and J. M. Harris and S. Zalipsky, Chemistry and Biological Applications of Polyethylene Glycol, ACS Books, Washington, D.C., 1997 and in U.S. Pat. No. 5,643,575).

Figure 2:
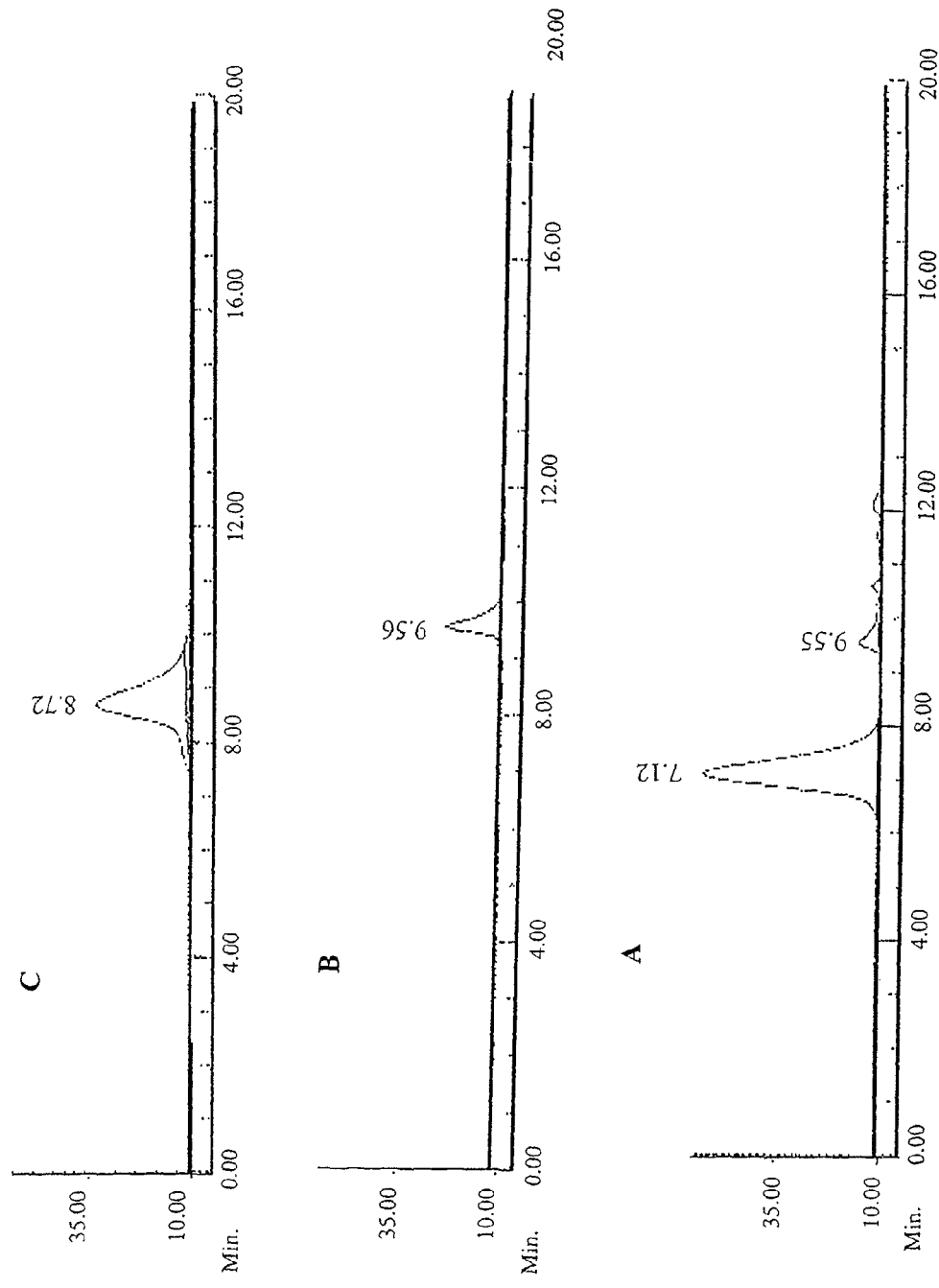
FIG. 2 shows an increase in molecular weight of the PTX-BBN[7-13]-BTN/SaV MDML conjugate described in FIG. 1A. Aliquots of the synthetic reaction described in FIG. 1A were taken (A, sample of streptavidin added at step h; B, aliquot of compound 9; C, aliquot of compound 10) and analyzed by SE-HPLC.

The synthesis of the PTX-BBN[7-13]-BTN/SaV conjugate using lysine as the core molecule is illustrated in FIG. 1A. The procedure is initiated with the synthesis of the 7-amino acid bombesin analog BBN[7-13] (SEQ ID NO. 1). BBN[7-13], 1, was synthesized by SPPS and through a fluorenyl methoxycarbonyl (Fmoc) protocol (Synpep, Synpep, CA). Peptide 1 was coupled to PEG to produce compound 2. Boc-lysine, 3, was condensed with PEG to produce compound 4. Compounds 2 and 4 were coupled together to produce compound 5. The product 5 was treated with piperidine/DMF, and was coupled to BTN-(sulfo)NHS to afford compound 6. Compound 6 was treated with TFA yield compound 7, which was coupled to PEG to produce compound 8. After de-protection, compound 8 was mixed with PTX to produce compound 9. Compound 9 was then mixed with a 25 mol % of SaV at 4 degree Celsius and pH 5.0 with stirring for one hour. The final product 10 was purified by RP-HPLC and identified by SE-HPLC on a G3000 Pwxl column (TosoHaas, Montgomeryville, Pa.) pre-calibrated by molecular weight markers (Bio-Rad, Hercules, Calif.) (FIG. 2). As can be seen in FIG. 2C, the final product, compound 10, has a higher molecular weight (indicated by shorter retention times on the SE-HPLC column) than the un-reacted SaV (FIG. 2A) or compound 9 (FIG. 2B), indicating the synthesis was successful.

Figure 1B:
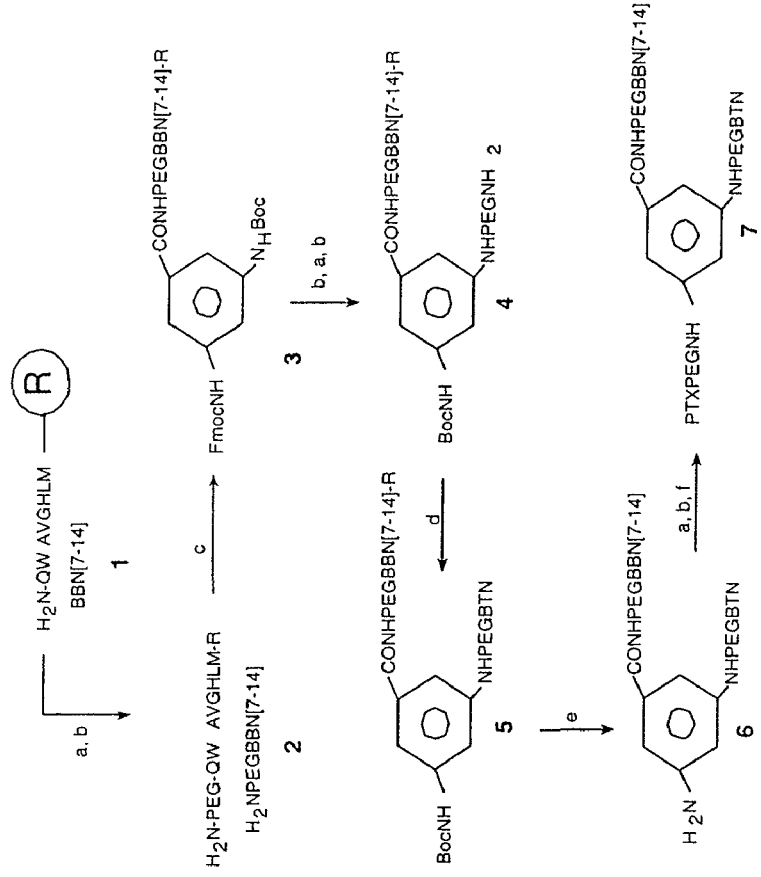

The synthesis of the PTX-BBN[7-14]-BTN/SaV conjugate using diamino benzoic acid as the core molecule is illustrated in FIG. 1B. Diamino benzoic acid is a planar molecule with an central aromatic phenyl ring having a 1, 3, 5 substitution pattern, which may reduce steric hindrance among the attached substituents. All coupling and deprotection steps shown in this scheme are of standard procedures. All intermediate and final products are identified by standard analytical and spectroscopic methods (NMR, mass spectroscopy, microanalysis, etc.). Solvents used are N,N-dimethyl formamide (DMF) and methylene chloride (DCM). Trifluoroacetic acid (TFA) and piperidine in DMF were used for deprotection of the Boc and Fmoc groups, respectively. The procedure is initiated with the synthesis of the 8-amino acid bombesin analog BBN[7-14] (SEQ ID NO. 2) 1 as described above. Peptide 1 is then connected to the central phenyl ring of diamino benzoic acid through active-ester chemistry using N,N-dicyclohexyl carbodiimide (DCC). The N-Boc-N'-Fmoc-3,5-diamino benzoic acid used in this reaction has been made in our laboratory through standard protocols. The resulting compound (3) undergoes two deprotection/coupling reactions to the commercially available Fmoc-PEG-NHS and biotin, respectively, afford the precleavage conjugate 5. The latter product is the cleaved from the resin, with concomitant removal of the Boc group by TFA to give 6. After purification by reversed-phase high-performance liquid chromatography (RP-HPLC), compound 6 is coupled to a third molecule of the Fmoc-PEG-NHS linker, which after removal of the Fmoc, is coupled to paclitaxel for afford the final product 7.

Example 2

Cell Proliferation Assay

To evaluate the growth inhibitory effects of the PTX-BBN [7-13]-BTN/SaV conjugate, experiments were designed to compare the effect of the conjugate with the unconjugated paclitaxel, the BTN/SaV complex and a mixture of free PTX and the BTN/SaV complex (FIG. 5). The low-receptor density NCI-H1299 non-small cell lung cancer cells were used to demonstrate the extent of the sensitivity of a native, untransfected cell line to treatment with the conjugate.

The HI299 cells were plated in 24 well plates at a density of 10,000 cells/well and allowed to adhere for 24 hours. The cells were treated with 50 nM of the following: 1) no treatment (Untreated); 2) unconjugated paclitaxel (PTX); 3) biotin/streptavidin complex (BTN/SaV); 4) a mixture of BTN/SaV and PTX; and 5) the PTX-BBN[7-13]-BTN/SaV conjugate (Conjugate) described in FIG. 1A. The drugs were removed from the cell monolayer after 3 hours and replaced with drug-free medium. After 96 hours, the cells were removed from the 24 well plates by treatment with trypsin/EDTA and counted with a Coulter particle counter. All treatments were done in quadruplicate and the cell counts were normalized to the untreated cells.

The PTX-BBN[7-13]-BTN/SaV conjugate demonstrated 37% growth inhibition compared to 0% growth inhibition by free PTX, and 1% and 4% inhibition by BTN/SaV and BTN/SaV+PTX controls, respectively. The results indicate that the PTX-BBN[7-13]-BTN/SaV was effective at inhibiting cell growth in the NIH HI299 cells where free PTX was not effective, suggesting the increased targeting and increased drug delivery of the PTX-BBN[7-13]-BTN/SaV MDML conjugate provided enhanced cell inhibition.

Example 3

Apoptosis Induction Assay

To evaluate the apoptosis-inducing ability of the PTX-BBN[7-13]-BTN/SaV conjugate, experiments were designed to compare the effect of the conjugate with the unconjugated paclitaxel, the BTN/SaV complex and a mixture of free PTX and the BTN/SaV complex (FIG. 6). The low-receptor density NCI-H1299 non-small cell lung cancer cells were used to demonstrate the extent of the sensitivity of a native, untransfected cell line to treatment with the conjugate.

The HI299 cells were plated in 24 well plates at a density of 10,000 cells/well and allowed to adhere for 24 hours. The cells were treated with 50 nM of the following: 1) no treatment (Untreated); 2) unconjugated paclitaxel (PTX); 3) biotin/streptavidin complex (BTN/SaV); 4) a mixture of BTN/SaV and PTX; and 5) the PTX-BBN[7-13]-BTN/SaV conjugate (Conjugate) described in FIG. 1A. The drugs were removed from the cell monolayer after 3 hours and replaced with drug-free medium. After 96 hours, the cells were removed from the 24 well plates by treatment with trypsin/EDTA and analyzed for Annexin V by flow cytometry using an Annexin V-FITC kit (Biovision, Palo Alto, Calif.). All treatments were done in triplicate and presented as the percentage of cells staining with Annexin V-FITC.

The PTX-BBN[7-13]-BTN/SaV conjugate showed a 7% induction of apoptosis, as compared to about 2.0%. 2.3%, 2.5% and 2.4% induction for untreated cells, free PTX, the BTN/SaV complex and the BTN/SaV complex+PTX controls, respectively. The results indicate that the PTX-BBN[7-13]-BTN/SaV was effective at inducing apoptosis in the NIH HI299 cells where free PTX was not effective, suggesting the increased targeting and increased drug delivery of the PTX-BBN[7-13]-BTN/SaV MDML conjugate provided enhanced cellular apoptosis.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present disclosure is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the disclosure.

What is claimed:

1. A method of targeting a therapeutic compound to an individual having cancer, the method comprising the step of administering to the individual a compound comprising a plurality of tripartite molecules linked to a scaffold moiety, with each tripartite molecule comprising a targeting molecule for directing the compound to a defined population of cells, a therapeutic agent and a scaffold binding element capable of complementary interaction with the scaffold moiety, each of the targeting molecule, the therapeutic agent and the scaffold binding element being joined by a linker molecule to a central core molecule, wherein the central core molecule is independently selected from the group consisting of lysine and diamino benzoic acid, the scaffold moiety is selected from the group consisting of avidin and streptavidin, the scaffold binding element is biotin, the linker molecule is polyethylene glycol and the targeting molecule is a peptide independently selected from the group consisting of SEQ ID NO: 1, SEQ ID NO: 2 and SEQ ID NO: 3 and the therapeutic agent is independently selected from the group consisting of paclitaxel, toxotere, a drug, an anti-tumor agent, a toxin, a radionuclide, and a metallic nuclei.

2. The method of claim 1 wherein the therapeutic agent is selected from the group consisting of paclitaxel and toxotere.

3. The method of claim 1 wherein said therapeutic compound is administered by injection of intravenous infusion.

4. The method of claim 2 wherein the peptide has the sequence selected from the group consisting of SEQ ID NO. 1, SEQ ID NO. 2 and SEQ ID NO. 3.

5. The method of claim 1 wherein the therapeutic agent is independently selected from the group consisting of a drug, an anti-tumor agent, a toxin, a radionuclide, and a metallic nuclei.

6. The method of claim 1 wherein the linker molecule has at least one of the properties selected from the group consisting of solubility in organic solutions, solubility in aqueous solutions, lack of immunogenicity and long half life in the bloodstream.

7. The method of claim 1 wherein the polyethylene glycol molecule is at least about 3400 molecular weight.

8. The method of claim 1 wherein the polyethylene glycol molecule contains at least two reactive groups.

9. The method of claim 1 wherein the targeting molecule is the BBN[7-13] peptide of SEQ ID NO: 1, the therapeutic agent is paclitaxel, the linker molecule is polyethylene glycol, the core molecule is lysine, the scaffold binding element is biotin and the scaffold moiety is streptavidin.

10. The method of claim 1 wherein the targeting molecule is the BBN[7-13] peptide of SEQ ID NO: 1, the therapeutic agent is paclitaxel, the linker molecule is polyethylene glycol, the core molecule is diamino benzoic acid, the scaffold binding element is biotin and the scaffold moiety is streptavidin.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Homo sapiens

<400> SEQUENCE: 1

Gln Trp Ala Val Gly His Leu
1               5

<210> SEQ ID NO 2
<211> LENGTH: 8
<212> TYPE: PRT
<213> ORGANISM: Homo sapiens

<400> SEQUENCE: 2

Gln Trp Ala Val Gly His Leu Met
1               5

<210> SEQ ID NO 3
<211> LENGTH: 10
<212> TYPE: PRT
<213> ORGANISM: Artificial
<220> FEATURE:
<223> OTHER INFORMATION: synthetic amino acid sequence based on the
      sequence of bombesin from homo sapien
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
```

```
<223> OTHER INFORMATION: Xaa can be any naturally occurring amino acid

<400> SEQUENCE: 3

Gly Xaa Gln Trp Ala Val Xaa His Phe Xaa
1               5                   10
```